United States Patent
Wagner et al.

(10) Patent No.: US 10,315,364 B2
(45) Date of Patent: Jun. 11, 2019

(54) METHOD FOR JOINING A PLURALITY OF WORKPIECE PARTS AND JOINING TOOL

(71) Applicant: Bayerische Motoren Werke Aktiengesellschaft, Munich (DE)

(72) Inventors: Julia Wagner, Garching (DE); Maximilian Wilhelm, Bockhorn (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 0 days.

(21) Appl. No.: 15/342,193

(22) Filed: Nov. 3, 2016

(65) Prior Publication Data
US 2017/0066184 A1    Mar. 9, 2017

Related U.S. Application Data

(63) Continuation of application No. PCT/EP2015/055427, filed on Mar. 16, 2015.

(30) Foreign Application Priority Data

May 7, 2014   (DE) .......................... 10 2014 208 512

(51) Int. Cl.
| | | |
|---|---|---|
| *B32B 41/00* | (2006.01) | |
| *B29C 65/82* | (2006.01) | |
| *B29C 65/60* | (2006.01) | |
| *B29C 65/00* | (2006.01) | |
| *G01N 29/04* | (2006.01) | |
| *G01N 29/14* | (2006.01) | |

(Continued)

(52) U.S. Cl.
CPC .......... *B29C 65/8292* (2013.01); *B29C 65/08* (2013.01); *B29C 65/602* (2013.01);
(Continued)

(58) Field of Classification Search
CPC ............... B29C 65/8292; B29C 65/08; B29C 66/81431; B29C 65/82; B29C 65/603;
(Continued)

(56) References Cited

U.S. PATENT DOCUMENTS 5,260,766 A * 11/1993 Armitage ................ B29C 65/18
                                                                    219/604
2006/0163213 A1    7/2006 Stieglbauer et al.
(Continued)

FOREIGN PATENT DOCUMENTS

| CN | 1678422 A | 10/2005 |
|---|---|---|
| CN | 101965507 A | 2/2011 |

(Continued)

OTHER PUBLICATIONS

Chinese Office Action issued in counterpart Chinese Application No. 201580005001.8 dated Apr. 14, 2017 with English translation (14 pages).

(Continued)

*Primary Examiner* — Michael N Orlando
*Assistant Examiner* — Joshel Rivera
(74) *Attorney, Agent, or Firm* — Crowell & Moring LLP

(57) ABSTRACT

A method is provided for joining a plurality of workpiece parts, in particular body parts, in which: a) the workpiece parts are inserted into a joining tool, b) the workpiece parts in the joining tool are monitored for damages, c) the workpiece parts are joined by the joining tool, and d) the joined workpiece is monitored for damages in the joining tool.

19 Claims, 1 Drawing Sheet

(51) Int. Cl.
*G01N 29/26* (2006.01)
*B29C 65/08* (2006.01)
*B29L 31/30* (2006.01)

(52) U.S. Cl.
CPC ............ *B29C 65/603* (2013.01); *B29C 65/82* (2013.01); *B29C 65/8261* (2013.01); *B29C 66/1122* (2013.01); *B29C 66/21* (2013.01); *B29C 66/41* (2013.01); *B29C 66/721* (2013.01); *B29C 66/81423* (2013.01); *B29C 66/81431* (2013.01); *B29C 66/8322* (2013.01); *G01N 29/043* (2013.01); *G01N 29/14* (2013.01); *G01N 29/262* (2013.01); *B29C 66/8124* (2013.01); *B29L 2031/3005* (2013.01); *B29L 2031/3055* (2013.01); *G01N 2291/2638* (2013.01)

(58) Field of Classification Search
CPC ............ B29C 65/8261; B29C 66/8322; B29C 65/602; B29C 66/81423; B29C 66/721; B29C 66/41; B29C 66/21; B29C 66/1122; B29C 66/8124; G01N 29/262; G01N 29/14; G01N 29/043; G01N 2291/2638; B29L 2031/3005; B29L 2031/3055
USPC .......................... 156/64, 350, 351, 378, 379
See application file for complete search history.

(56) References Cited

U.S. PATENT DOCUMENTS

| | | | |
|---|---|---|---|
| 2007/0034313 A1* | 2/2007 | Engelbart | ............... B29C 70/32 |
| | | | 156/64 |
| 2009/0133501 A1* | 5/2009 | Georgeson | ............ G01N 29/04 |
| | | | 73/632 |
| 2010/0281964 A1 | 11/2010 | Lakrout et al. | |
| 2012/0310551 A1* | 12/2012 | Na | .................... G01N 29/0645 |
| | | | 702/39 |
| 2013/0269438 A1 | 10/2013 | Hepp | |

FOREIGN PATENT DOCUMENTS

| | | |
|---|---|---|
| DE | 198 34 797 C2 | 4/2002 |
| DE | 10 2011 089 475 A1 | 6/2012 |
| EP | 2 657 801 A2 | 10/2013 |
| JP | 2004-1071 A | 1/2004 |

OTHER PUBLICATIONS

International Search Report (PCT/ISA/210) issued in PCT Application No. PCT/EP2015/055427 dated May 29, 2015, with English translation (four (4) pages).
German-language Written Opinion (PCT/ISA/237) issued in PCT Application No. PCT/EP2015/055427 dated May 29, 2015 (six (6) pages).
German Office Action issued in counterpart German Application No. 10 2014 208 512.8 dated Jan. 21, 2015 (five (5) pages).
Chinese-language Office Action issued in counterpart Chinese Application No. 201580005001.8 dated Dec. 7, 2017 with English translation (13 pages).
Chinese-language Office Action issued in counterpart Chinese Application No. 201580005001.8 dated Jun. 14, 2018 with English translation (twelve (12) pages).

\* cited by examiner

METHOD FOR JOINING A PLURALITY OF WORKPIECE PARTS AND JOINING TOOL

CROSS REFERENCE TO RELATED APPLICATIONS

This application is a continuation of PCT International Application No. PCT/EP2015/055427, filed Mar. 16, 2015, which claims priority under 35 U.S.C. § 119 from German Patent Application No. 10 2014 208 512.8, filed May 7, 2014, the entire disclosures of which are herein expressly incorporated by reference.

BACKGROUND AND SUMMARY OF THE INVENTION

The invention relates to a method for joining a plurality of workpiece parts, particularly of vehicle body components, as well as to a joining tool.

For checking the quality of the joining points of a workpiece formed of a plurality of workpiece parts, for example, of a vehicle body component, a nondestructive examination, at least in the manner of spot checking, is an absolute necessity. In the field of vehicle body construction, a nondestructive examination of joined workpieces takes place subsequent to the production. For this purpose, a vehicle selected at random is usually removed and is examined manually. However, the joined workpieces or joining points of each vehicle are never all examined, but the nondestructive examination is always only carried out on individual vehicles and at individual joining points.

In the field of vehicle body construction, the use of fiber-reinforced plastic materials is increasing. In contrast to the joining of workpiece parts made of steel, the joining of workpiece parts made of fiber-reinforced plastic is more complex and has higher reject rates. In order to be able to continue to guarantee a high degree of quality, the number of spot checks has to be increased which results in higher cost and is more time consuming.

It is an object of the invention to provide a possibility for examining joined workpieces that can be integrated into the production without high expenditures of cost and time.

This object is achieved by a method for joining a plurality of workpiece parts, particularly of vehicle body components, wherein a) the workpiece parts are inserted into a joining tool;

b) the workpiece parts in the joining tool are checked for damage;

c) the workpiece parts are joined by the joining tool; and d) the joined workpiece is checked for damage in the joining tool.

By examining the workpiece parts and the checked workpiece in the joining tool itself, it becomes possible to examine the workpiece parts and the joined workpiece respectively for damage without requiring large expenditures of time. In addition, each of the workpiece parts to be joined and each of the joined workpieces can be examined, so that, in contrast to random-type testing, quality control of the workpieces is clearly improved.

The workpiece parts can be examined just before the joining and the joined workpiece can be examined immediately after the joining, particularly by a testing device provided in the joining tool, so that newly occurring damage will undoubtedly be the result of the joining.

For example, at least one of the plurality of workpiece parts may be made of a fiber-reinforced plastic material, so that the joined workpiece part can gain the advantages of fiber-reinforced plastic material.

When critical damage to one of the workpiece parts or to the joined workpiece was detected, this workpiece part or the joined workpiece is preferably separated out, so that components with excessive damage will be detected as early as possible and will no longer be used. Typical damages in fiber-reinforced plastic caused during the joining are delamination or inter-fiber failures.

In an embodiment, damage to the workpiece parts before the joining is compared with damage to the joined workpiece after the joining; the damage caused by the joining is determined and the joined workpiece is separated out if the damage caused by the joining is critical. As a rule, the workpiece parts used in automobile body construction already have a certain degree of irregularities, for example, as a result of the placing of holes. It is therefore not possible to set an absolute damage limit as critical for the quality control of a joined workpiece. By comparing the damage to the workpiece parts before the joining and the damage to the joined workpiece part, a conclusion can be drawn concerning damage caused by the joining itself, so that this damage can be assessed separately. In this manner, the assessment of the damage caused by the joining will become significantly more differentiated. In this case, a damage is considered to be critical, for example, if the damage caused by the joining exceeds to a critical extent the magnitude of the irregularities before the joining, particularly if the irregularities classified as not critical before the joining has increased more than two-fold as a result of the damage produced by the joining. Particularly the ratio of magnitudes of the irregularities before the joining to the damage after the joining with respect to one another can also be defined as the limit value.

In a further development of the invention, the workpiece parts and/or the joined workpiece are tested by use of air ultrasound, contact ultrasound, acoustic emission, thermography and/or another nondestructive method. These methods have been tested and are known, so that their use is cost-effective.

In an embodiment of the invention, the joining tool has a die and a die plate, the workpiece parts being examined for damage when the die is disposed on the workpiece part, and/or the joined workpiece is examined for damage when the joining tool is completely closed. In this manner, a fully automated and time-saving examination of the workpiece parts and/or of the joined workpiece becomes possible.

In an embodiment, in the case of one-sided joining methods, the workpiece parts can be examined for damage when the die is disposed on one of the workpiece parts or is positioned at a distance of less than 3.0 mm from one of the workpiece parts. In this manner, the workpiece part can also be examined without any contact.

For example, before Step b) a coupling agent between the die and one of the workpiece parts is supplied in an automated manner, whereby the quality of the examination is improved.

After Step d) the coupling agent between the die and the workpiece is preferably removed in an automated manner, so that the joined workpiece will be free of coupling agent residue.

The evaluation as to whether damage is critical can take place in an automated manner, particularly by comparing the samples obtained during the tests with one another and/or with a limit sample, whereby the personal expenditures for the examination and thereby the occurring costs can be considerably reduced. The comparison of the obtained samples with one another or with a limit sample can take place by way of image processing software, in which case the magnitude of the differences between the obtained samples with one another or between the samples and the limit sample can be used for measuring the damage.

In a further development of the invention, the samples obtained during the examination, together with information concerning the final product, such as the chassis number in the case of vehicles, in which the joined workpiece was installed, are stored in a databank. In this manner, it becomes possible to prove the quality of the joined workpiece, in the event of future claims that may be alleged by a buyer.

The object is further achieved by a joining tool for joining a plurality of workpiece parts, particularly workpiece parts made of a fiber-reinforced plastic material, with at least one testing device, which is constructed on a workpiece contact surface of the joining tool and can examine the workpiece to be joined with respect to damages. By use of the joining tool, it also becomes possible to carry out an examination of the workpiece parts and/or of the joined workpiece without additional transport steps of the workpiece parts and/or of the joined workpiece.

The testing device is preferably constructed for the testing by use of air ultrasound, contact ultrasound, acoustic emission and/or another nondestructive method. In particular, the testing device is a phased array ultrasonic probe, permitting the use of known cost-effective and high-quality testing devices.

The joining tool may be a forming tool having a die and a die plate. It may, in particular, be a semi-tubular punch riveter, in which case, the at least one testing device is provided in the die and/or in the die plate, so that a testing of the workpiece parts and/or of the workpiece can take place directly in the production facility.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
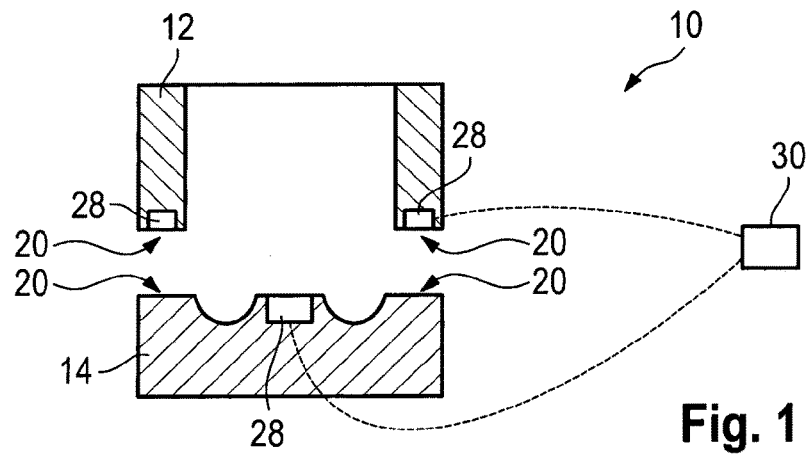
FIG. 1 is a sectional view of a joining tool according to an embodiment of the invention in the open position.

FIG. 1 is a schematic sectional view of a joining tool 10 for joining a plurality of workpiece parts, particularly vehicle body components.

The joining tool 10 may be a forming tool, for example, a semi-tubular punch riveter.

The joining tool 10 for joining workpiece parts may also be constructed of fiber-reinforced plastic material.

The joining tool 10 has a die 12 and a die plate 14, the die 12 being displaceable with respect to the die plate 14.

Figure 3:
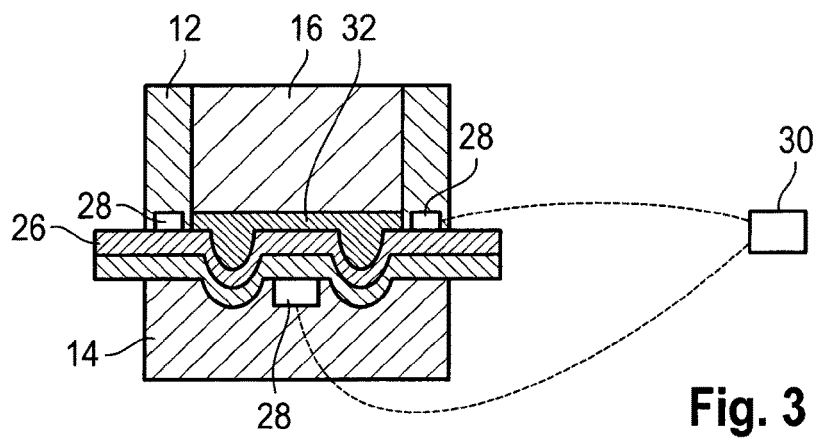
FIG. 3 is a view of the joining tool according to FIG. 1 in the completely closed position.

The die 12 has a cylindrical and, for example, hollow construction and is used for guiding a bolt 16 (FIG. 3).

The surface of the die 12 facing the die plate as well as the side of the die plate 14 facing the die 12 form workpiece contact surfaces 20 on which the workpiece parts 22, 24 (FIG. 2) to be joined or the joined workpiece 26 (FIG. 3) come to rest when the joining tool 10 is used.

At least one testing device 28 is provided on the workpiece contact surfaces 20 on the die 12 as well as on the die plate 14.

The testing device 28 is designed for examination by air ultrasound, contact ultrasound, acoustic emission and/or another nondestructive method.

The testing device 28, for example, is a phased array ultrasonic probe.

It is naturally also contemplated for a testing device 28 to be provided only on the die 12 or only on the die plate 14.

In addition, the size, position and/or orientation of the testing devices 28 are the result of the geometry of the workpiece contact surfaces 20 and of the workpiece parts 22, 24 to be examined or of the joining points.

The testing devices 28 are connected with an analysis unit 30, for example, a microprocessor-based control unit of the joining tool 10. This is outlined in the drawings by a broken line.

Together with the analysis unit 30, the testing device 28 can examine the workpiece parts 22, 24 to be joined and/or the joined workpiece 26 for damage.

For joining a plurality of workpieces 22, 24, the workpiece parts 22, 24 to be joined are inserted into the joining tool 10. In this case, at least one of the workpiece parts 22, 24 can be made of a fiber-reinforced plastic material.

A coupling agent (not shown), for example, a contact gel, can now be supplied in an automated manner between the die 12 and one of the workpiece parts 22, 24.

Figure 2:
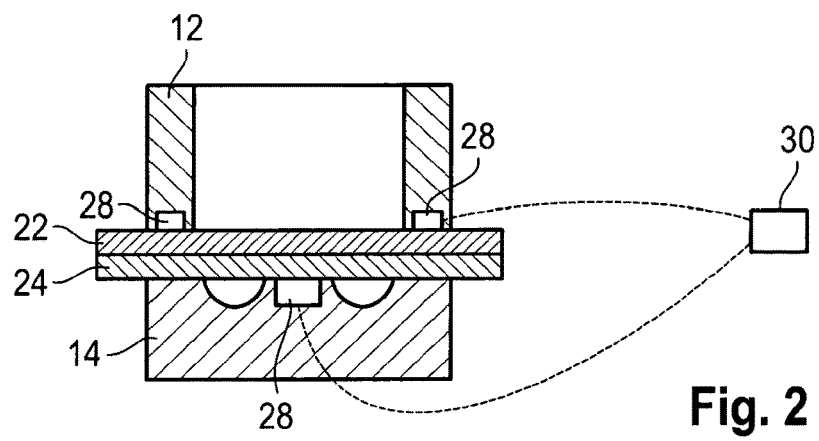
FIG. 2 is a view of the joining tool according to FIG. 1 with inserted workpiece parts.

The applied coupling agent can be removed in an automated manner after the joining. The joining tool 10 will now be closed to such an extent that the die 12 is disposed on the workpiece part 22 that is closer to it. This position is illustrated in FIG. 2. In this position, the testing devices 28 now rest against the workpiece parts 22 and 24, respectively, and can test the workpiece parts 22, 24 in the joining tool 10 for damage.

The examination of the workpiece parts 22, 24 therefore takes place just before the joining.

The checking of the workpiece parts 22, 24 and, subsequently, of the joined workpiece 26 takes place by way of air ultrasound, contact ultrasound, acoustic emission, thermography and/or another nondestructive method.

In the event that the testing devices 28 are phased array ultrasonic probes, for example, a sample of the checked workpiece part 22, 24 is obtained by the testing, which can then be transmitted to the analysis unit 30.

The samples of the workpiece parts 22, 24 obtained during the testing are placed in the analysis unit 30.

An assessment as to whether damage, i.e. an irregularity of the workpiece parts 22, 24, is critical may be carried out, for example, in that the obtained sample is compared with a limit sample, which is stored in the memory of the analysis unit 30, and the damage will be considered critical if the obtained sample differs from the corresponding limit sample beyond a defined extent.

This assessment can be carried out by the analysis unit 30 in an automated manner.

When critical damage is detected in the case of one of the workpiece parts 22, 24, this workpiece part 22, 24 will be separated out.

This means that the joining tool 10 is opened up again and the damaged workpiece part 22, 24 is removed and replaced.

When the two workpiece parts 22, 24 have no critical damage, the workpiece parts 22, 24 will be joined by the joining tool 10.

In the illustrated embodiment, a rivet 32 is introduced into the workpiece parts 22, 24 by means of a bolt 16, as shown in FIG. 3.

In this manner, the joined workpiece 26 is obtained which consists of the two workpiece parts 22, 24.

The position of the joining tool 10 illustrated in FIG. 3 corresponds to the completely closed position, in which the joined workpiece 26 is checked for damage by the testing devices 28.

The examination of the joined workpiece 26 therefore takes place immediately after the joining.

The samples obtained during the examination of the joined workpiece 26 can also be transmitted to the analysis unit 30, in which they are compared with a limit sample for joined workpieces, which is stored in the analysis unit 30.

When the sample obtained during the examination deviates excessively from the limit sample, a conclusion is drawn that the damage to the joined workpiece 26 is critical and the joined workpiece 26 is separated out, which means that it will no longer be used.

Also, the samples of the individual workpiece parts 22, 24 can be compared in the analysis unit 30 with the sample of the joined workpiece 26, and a conclusion can be drawn from the differences of the samples as to the damage resulting from the joining.

The comparison of the obtained samples with one another and/or with a limit sample can take place by use of image processing software, in which case the magnitude of the differences between the obtained samples with respect to one another or between the obtained samples and the limit sample can be used for measuring the damage.

If the damage caused during the joining exceeds a predefined limit, the joined workpiece 26 will also be separated out. Particularly, the ratio of magnitudes of the two damage cases with respect to one another can be defined as the limit value.

For example, damage will be considered to be critical when the damage caused by the joining exceeds the magnitude of the initial damage to a critical extent, particularly when the initial damage, classified as non-critical, has increased in its magnitude more than two-fold as a result of the damage caused by the joining.

Typical damages in fiber-reinforced plastic material caused during joining are delamination or inter-fiber failures.

The obtained sample of the joined workpiece 26 can also be stored in the analysis unit 30.

In addition, the obtained sample of the joined workpiece 26 together with the samples of the individual workpiece parts 22, 24 can be stored in a database and can be linked to information concerning the final product in which the joined workpiece 26 was used. The information concerning the product may, for example, be the chassis number of the vehicle in which the joined workpiece 26 was installed, so that, in the event of later claims, the samples of the workpiece parts 22, 24 and of the joined workpiece can be used.

It is naturally also contemplated that the joining tool 10 is a different joining tool than the illustrated semi-tubular punch riveter.

Naturally, also more than the illustrated two workpiece parts can be mutually connected without deviating from the idea of the invention.

It is also contemplated that, in the case of one-sided joining methods, the joining tool 10 checks the workpiece parts 22, 24 for damage when the die 12 is disposed on one of the workpiece parts 22, 24 or is positioned at a distance of less than 3.0 mm from one of the workpiece parts 22, 24.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for joining a plurality of workpiece parts, the method comprising the steps of:
    a) inserting the workpiece parts into a joining tool;
    b) checking the workpiece parts to be joined for damage by a testing device provided in the joining tool while the workpiece parts to be joined are in the joining tool prior to a joining process;
    c) joining the workpiece parts by the joining tool; and
    d) checking the joined workpiece for damage by the testing device while the joined workpiece is in the joining tool, wherein
    the testing device is configured to check both the damage of the workpiece parts to be joined and the damage of the joined workpiece while the workpiece parts prior to the joining process and the joined workpiece are in the joining tool without requiring additional transport steps.

2. The method according to claim 1, wherein the workpiece parts are vehicle body components.

3. The method according to claim 1, wherein the workpiece parts are checked just before the joining and the joined workpiece is checked immediately after the joining.

4. The method according to claim 1, wherein at least one of the plurality of workpiece parts is made of a fiber-reinforced plastic material.

5. The method according to claim 1, wherein when critical damage to one of the workpiece parts or to the joined workpiece is detected, separating out the critically damaged workpiece part or the critically damaged joined workpiece.

6. The method according to claim 1, further comprising the steps of:
    comparing damage to the workpiece parts before the joining with damage to the joined workpiece after the joining;
    determining damage caused by the joining of the workpiece parts; and
    separating-out the joined workpiece if the damage caused by the joining is critical.

7. The method according to claim 1, wherein at least one of the checking steps is carried out via air ultrasound, contact ultrasound, acoustic emission, thermography, and/or another non-destructive method.

8. The method according to claim 1, wherein:
    the joining tool comprises a die and a die plate, and
    the workpiece parts are checked for damage when the die is disposed on one of the workpiece parts and/or the joined workpiece is checked for damage when the joining tool is completely closed.

9. The method according to claim 1, wherein:
    the joining tool comprises a die, and
    the joining tool checks the workpiece parts for damage when the die is disposed on one of the workpiece parts or is positioned at a distance of less than 3.0 mm from one of the workpiece parts.

10. The method according to claim 8, wherein, before step b), a coupling agent is supplied in an automated manner between the die and one of the workpiece parts.

11. The method according to claim 9, wherein, before step b), a coupling agent is supplied in an automated manner between the die and one of the workpiece parts.

12. The method according to claim 10, wherein, after step d), the coupling agent between the die and the joined workpiece is removed in an automated manner.

13. The method according to claim 11, wherein, after step d), the coupling agent between the die and the joined workpiece is removed in an automated manner.

14. The method according to claim 1, wherein an assessment as to whether damage is critical occurs in an automated manner by comparing samples with one another and/or with a limit sample.

15. The method according to claim 14, wherein the samples, together with information concerning a final product in which the joined workpiece is used, are stored in a database.

16. A joining tool for joining a plurality of workpiece parts made of a fiber-reinforced plastic material, comprising:

at least one testing device constructed on one workpiece contact surface of the joining tool, wherein the testing device is configured to check the workpiece parts to be joined for damage while the workpiece parts to be joined are in the joining tool prior to a joining process, and the testing device is configured to check the joined workpiece for damage while the joined workpiece is in the joining tool, wherein the testing device is configured to check both the damage of the workpiece parts to be joined and the damage of the joined workpiece while the workpiece parts prior to the joining process and the joined workpiece are in the joining tool without requiring additional transport steps.

17. The joining tool according to claim 16, wherein the testing device is configured to test via air ultrasound, contact ultrasound, acoustic emission, and/or another non-destructive testing method.

18. The joining tool according to claim 16, wherein the testing device is a phased array ultrasonic probe.

19. The joining tool according to claim 16, wherein the joining tool is a semi-tubular punch riveter having a die and a die plate, the testing device being provided in one or more of the die and the die plate.

* * * * *